United States Patent
Savage

(10) Patent No.: US 8,975,310 B2
(45) Date of Patent: Mar. 10, 2015

(54) HYDROPHOBIC CERAGENIN COMPOUNDS AND DEVICES INCORPORATING SAME

(75) Inventor: Paul B. Savage, Mapleton, UT (US)

(73) Assignee: Brigham Young University, Provo, UT (US)

(*) Notice: Subject to any disclaimer, the term of this patent is extended or adjusted under 35 U.S.C. 154(b) by 193 days.

(21) Appl. No.: 13/554,957

(22) Filed: Jul. 20, 2012

(65) Prior Publication Data
US 2013/0053507 A1 Feb. 28, 2013

Related U.S. Application Data

(60) Provisional application No. 61/572,714, filed on Jul. 20, 2011, provisional application No. 61/642,431, filed on May 3, 2012.

(51) Int. Cl.
| | | |
|---|---|---|
| *C07J 41/00* | (2006.01) | |
| *C08G 59/50* | (2006.01) | |
| *C08K 5/24* | (2006.01) | |
| *C09D 5/16* | (2006.01) | |
| *C07C 211/00* | (2006.01) | |
| *A61L 27/52* | (2006.01) | |
| *A61L 27/54* | (2006.01) | |
| *A61L 31/14* | (2006.01) | |
| *A61L 31/16* | (2006.01) | |
| *A61L 27/34* | (2006.01) | |
| *A61L 29/08* | (2006.01) | |
| *A61L 29/14* | (2006.01) | |
| *A61L 29/16* | (2006.01) | |
| *A61L 31/10* | (2006.01) | |

(52) U.S. Cl.
CPC .............. *C07C 211/00* (2013.01); *A61L 27/52* (2013.01); *A61L 27/54* (2013.01); *A61L 31/145* (2013.01); *A61L 31/16* (2013.01); *A61L 27/34* (2013.01); *A61L 29/085* (2013.01); *A61L 29/145* (2013.01); *A61L 29/16* (2013.01); *A61L 31/10* (2013.01); *A61L 2300/404* (2013.01)
USPC ........... 523/122; 524/243; 524/261; 524/265; 536/99; 536/123; 552/505; 552/553

(58) Field of Classification Search
USPC ............. 523/122; 552/505, 553; 536/99, 123; 524/243, 261, 265
See application file for complete search history.

(56) References Cited

U.S. PATENT DOCUMENTS

| | | | |
|---|---|---|---|
| 4,972,848 A | 11/1990 | Di Domenico | |
| 6,350,738 B1 | 2/2002 | Savage et al. | |
| 6,486,148 B2 | 11/2002 | Savage et al. | |
| 6,767,904 B2 | 7/2004 | Savage et al. | |
| 6,939,376 B2 | 9/2005 | Shulze et al. | |
| 7,282,214 B2 | 10/2007 | Wilcox et al. | |
| 7,598,234 B2 | 10/2009 | Savage et al. | |
| 7,754,705 B2 | 7/2010 | Savage et al. | |
| 8,211,879 B2 | 7/2012 | Savage et al. | |
| 8,623,416 B2 | 1/2014 | Zasloff et al. | |
| 8,784,857 B2 | 7/2014 | Savage | |
| 2005/0032765 A1 | 2/2005 | Savage et al. | |
| 2005/0075321 A1* | 4/2005 | Ahlem et al. | ................. 514/172 |
| 2005/0244468 A1 | 11/2005 | Huang et al. | |
| 2006/0269485 A1 | 11/2006 | Friedman et al. | |
| 2007/0106393 A1 | 5/2007 | Miles et al. | |
| 2007/0190066 A1 | 8/2007 | Savage et al. | |
| 2007/0190067 A1* | 8/2007 | Savage et al. | .............. 424/160.1 |
| 2007/0190558 A1 | 8/2007 | Savage et al. | |
| 2008/0188819 A1 | 8/2008 | Kloke et al. | |
| 2010/0330086 A1 | 12/2010 | Savage et al. | |
| 2011/0123624 A1 | 5/2011 | Zasloff | |
| 2013/0022651 A1 | 1/2013 | Savage | |
| 2013/0243823 A1 | 9/2013 | Genberg et al. | |
| 2013/0243840 A1 | 9/2013 | Savage et al. | |
| 2013/0245760 A1 | 9/2013 | Savage et al. | |

FOREIGN PATENT DOCUMENTS

| | | |
|---|---|---|
| WO | WO 9524415 | 9/1995 |
| WO | WO 9944616 | 9/1999 |
| WO | WO 0042058 | 7/2000 |
| WO | WO 0214342 | 2/2002 |
| WO | WO 03015757 | 2/2003 |
| WO | WO 2007089903 | 8/2007 |
| WO | WO 2007089906 | 8/2007 |
| WO | WO 2007089907 A2 * | 8/2007 |
| WO | WO 2009079066 | 6/2009 |
| WO | WO 2010036427 A1 * | 4/2010 |
| WO | WO 2011109704 | 9/2011 |
| WO | 2012-061651 | 5/2012 |
| WO | WO2013/109236 | 7/2013 |

OTHER PUBLICATIONS

P B Savage et al. "Thin Films Containing Ceragenins Prevent Biofilm Formation on Endotracheal Tubes", $9^{th}$ International Federation of Infection Control Congress, Oct. 14, 2008, pp. 1-1.
U.S. Appl. No. 14/288,126, filed May 27, 2014, Savage et al.
Xin-Zhong Lai, et al., "Ceragenins: Cholic Acid-Based Mimics of Antimicrobial peptides", Account of Chemical Research vol. 41, No. 10, Oct. 21, 2008, pp. 1233-1240.
K.D. Sinclair, et al., "Development of a broad spectrum polymer-released antimicrobial coating for the prevention of resistant strain bacterial infections", Journal of Biomedical Materials Research Part A, vol. 100A, No. 10, May 24, 2012, pp. 2732-2738.
Emily L. Perry et al., "Assessing peri-implant tissue infection prevention in a percutaneous model", Journal of Biomedical Materials Research Part B: Applied Biomaterials, vol. 02B, Nov. 19, 2009, pp. 397-408.
Savage, et al., "Antibacterial Activities of Thin Films Containing Ceragenins", Microbial Surfaces: Structure, Interactions and Reactivity, ACS, May 30, 2008, pp. 65-78.

(Continued)

Primary Examiner — Kriellion Sanders
(74) Attorney, Agent, or Firm — Workman Nydegger

(57) ABSTRACT

A hydrophobic cationic steroidal anti-microbial (ceragenin) compound forms an amphiphilic compound having a hydrophobic sterol face and a hydrophilic cationic face. The hydrophobic CSA also includes a hydrophobic substituent that gives the ceragenin compound a CLogP value of at least 6.5.

20 Claims, 12 Drawing Sheets

(56) References Cited

OTHER PUBLICATIONS

P. B. Savage, et al., "Use of a Ceragenin-Based Coating to Prevent Bacterial Colonization of Urinary Catheters", 48th Annual Interscience Conference on Anti-Microbial Agents & Chemotherapy, Oct. 26, 2008, pp. 1-1.

Michael D. Howell, et al., "Ceragenins: A 1-18, class of Antiviral Compounds to Treat Orthopox Infections", Journal of Investigative Dermatology, vol. 129, No. 11, Jun. 11, 2009, pp. 2688-2675.

K. Leszczynska et al., "Potential of ceragenin CSA-13 and its mixture with pluronic F-127 as treatment of topical bacterial infections", Journal of Applied Microbiology, vol. 110, No. 1, Oct. 21, 2010, pp. 229-238.

Isogai E et al: "Ceragenin CSA-13 exhibits antimicrobial activity against cariogenic and periodontopathic bacteria", Oral Microbiology and Immunology, vol. 24, No. 2, Apr. 2009, pp. 170-172.

Van Bambeke et al: "The bacterial envelope as a target for novel anti-MRSA antibiotics", Trends in Pharmacological Sciences, Elsevier, Haywarth, GB, vol. 29, No. 3, Feb. 11, 2008, pp. 124-134.

Qunying Guan et al: "Preparation and Characterization of Cholic Acid-Derived Antimicrobial Agents with Controlled Stabilities", Organic Letters, American Chemical Society, US, vol. 2, No. 18, Sep. 7, 2000, pp. 2837-2840.

Alhanout K et al: "Squalamine as an example of a new potent antimicrobial agents class: a critical review.", Current Medicinal Chemistry 2010, vol. 17, No. 32, 2010, pp. 3909-3917.

U.S. Appl. No. 13/594,608, filed Jan. 30, 2014, Office Action.

U.S. Appl. No. 13/594,612, filed May 15, 2014, Office Action.

U.S. Appl. No. 13/615,324, Jan. 30, 2014, Office Action.

* cited by examiner

CSA-13
CLogP: 5.228

CSA-90
CLogP: 6.0858

CSA-44
CLogP: 6.351

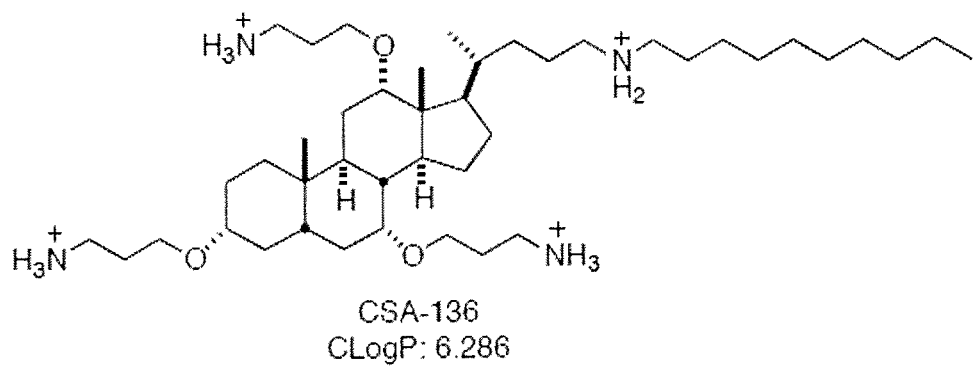
CSA-136
CLogP: 6.286
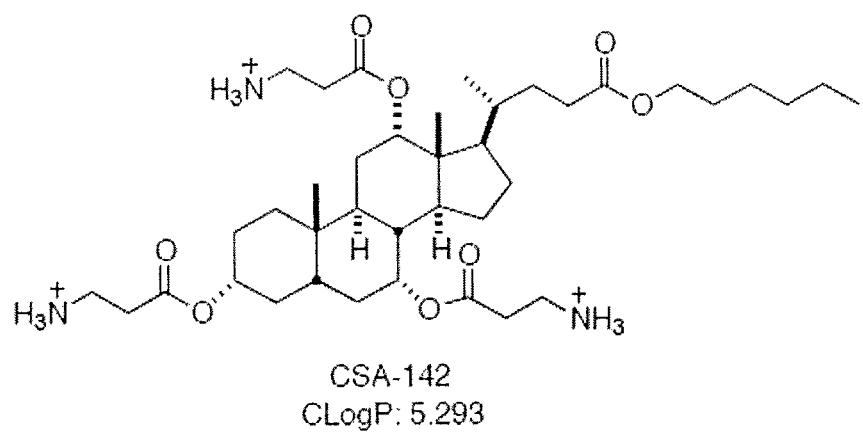
CSA-142
CLogP: 5.293
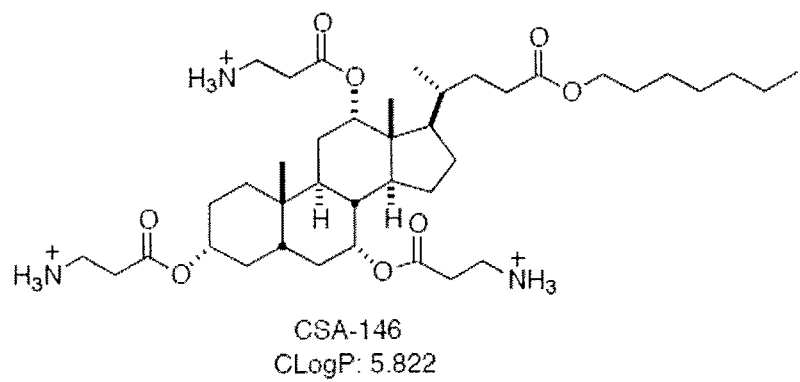
CSA-146
CLogP: 5.822
FIGURE 1A (con't)

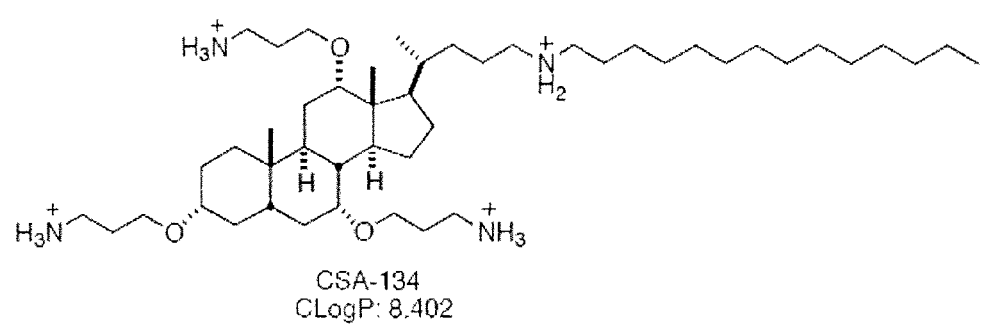
CSA-134
CLogP: 8.402
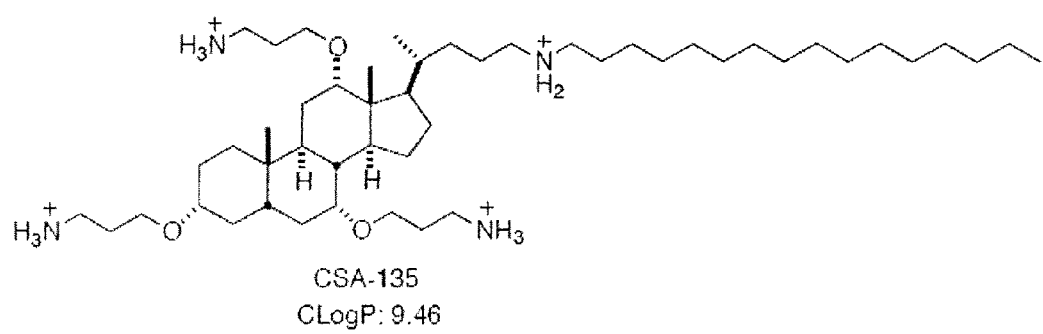
CSA-135
CLogP: 9.46
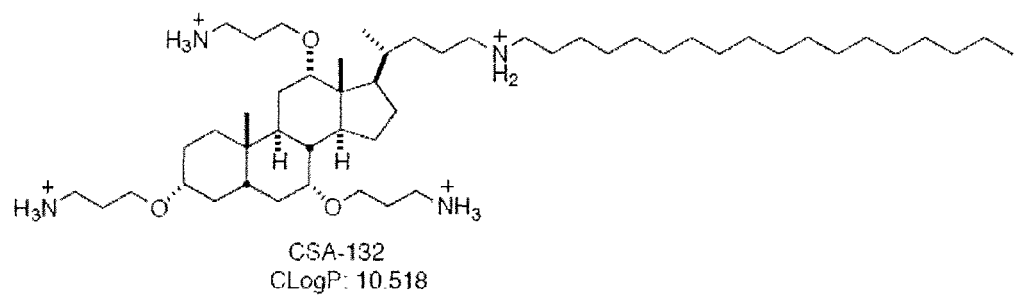
CSA-132
CLogP: 10.518
FIGURE 1B (con't)

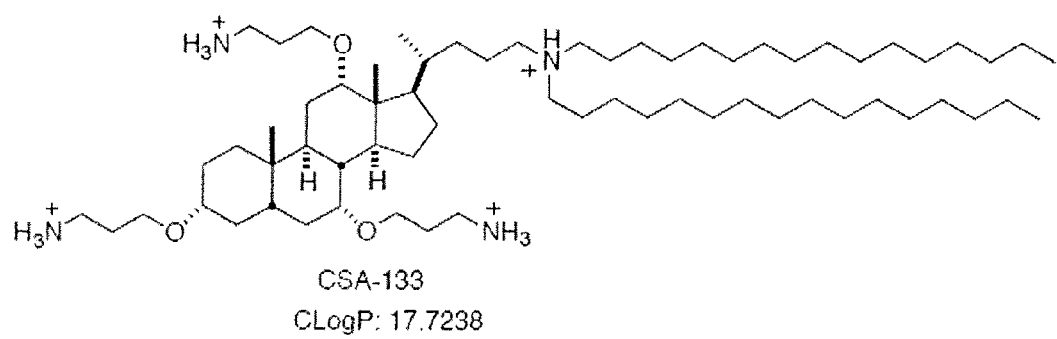
CSA-133
CLogP: 17.7238
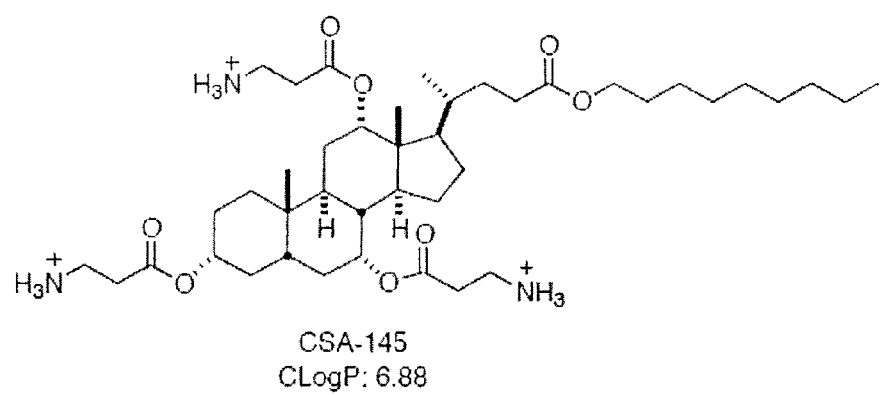
CSA-145
CLogP: 6.88
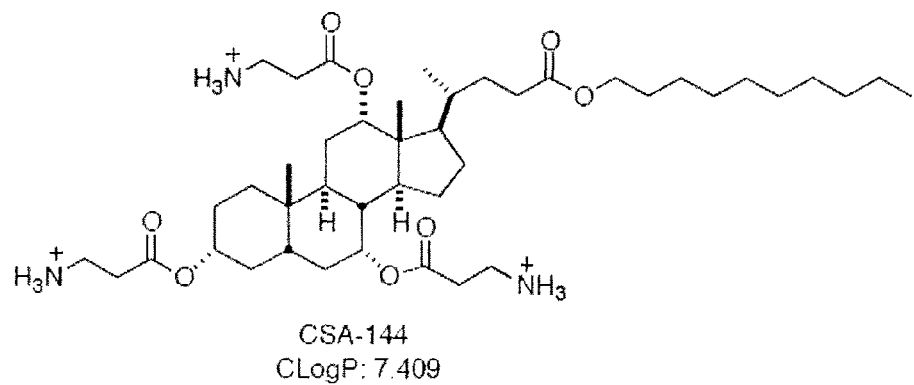
CSA-144
CLogP: 7.409
FIGURE 1B (con't)

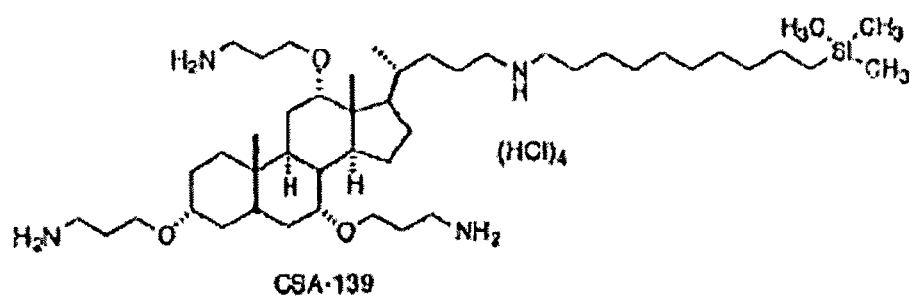
FIGURE 1B (con't)

HYDROPHOBIC CERAGENIN COMPOUNDS AND DEVICES INCORPORATING SAME

CROSS-REFERENCE TO RELATED APPLICATIONS

This application claims the benefit of U.S. Provisional application Nos. 61/572,714 filed Jul. 20, 2011, titled "Ceragenin-Containing Hydrogels For Prevention of Bacterial Biofilm Formation" and 61/642,431, filed May 3, 2012, titled Hydrogel Materials Incorporating Eluting Ceragenin Compound," both of which are hereby incorporated herein by reference.

BACKGROUND OF THE INVENTION

1. The Field of the Invention

The present invention relates to hydrophobic ceragenin compounds and devices incorporating the hydrophobic ceragenin compounds. The ceragenin compounds have hydrophobic substituents that give the compounds a relatively high CLogP value that allow the compounds to be non-covalently bonded to polymeric materials.

2. The Relevant Technology

Ceragenin compounds, also referred to herein as cationic steroidal anti microbial compounds (CSA), are synthetically produced small molecule chemical compounds that include a sterol backbone having various charged groups (e.g., amine and cationic substituents) attached to the backbone. The backbone can be used to orient the amine or guanidine groups on one face, or plane, of the sterol backbone. For example, a scheme showing a compound having primary amino groups on one face, or plane, of a backbone is shown below in Scheme I:

Scheme I $NH_2$ $NH_2$ $NH_2$

Ceragenins are cationic and amphiphilic, based upon the functional groups attached to the backbone. They are facially amphiphilic with a hydrophobic face and a polycationic face. Without wishing to be bound to any particular theory, the anti-microbial ceragenin compounds described herein act as anti-microbial agents (e.g., anti-bacterials, anti-fungals, and anti-virals). It is believed, for example, that the ant-microbial ceragenin compounds described herein act as anti-bacterials by binding to the outer cellular membrane of bacteria and other microbes and inserting into the cell membrane forming a pore that allows the leakage of ions that are critical to the microbe's survival and leading to the death of the affected microbe. In addition, the anti-microbial ceragenin compound described herein may also act to sensitize bacteria to other antibiotics. For example, at concentrations of the anti-microbial ceragenin compounds below the corresponding minimum bacteriostatic concentration, the ceragenins cause bacteria to become more susceptible to other antibiotics by increasing the permeability of the outer membrane of the bacteria.

The charged groups are responsible for disrupting the bacterial cellular membrane, and without the charged groups, the ceragenin compound cannot disrupt the membrane to cause cell death or sensitization.

BRIEF SUMMARY

The present invention relates to ceragenin compounds that are relatively hydrophobic despite having a hydrophilic cationic face. The high hydrophobicity has been found to have a surprising and unexpected ability to bond with polymers and then selectively release from the polymeric materials to kill microbes.

In one embodiment, hydrophobic ceragenin compounds disclosed herein have (i) a sterol structure comprising four fused carbon rings; (ii) at least one cationic substituent attached to each of at least three of the four fused carbon rings so as to form an amphiphilic compound having a hydrophobic sterol face and a hydrophilic cationic face; (iii) at least one hydrophobic substituent attached to at least one of the fused carbon rings; and (iv) wherein the CSA compound has a CLogP value of at least 6.5.

The CLogP value is achieved by selecting a proper hydrophobic substituent(s) in combination with proper cationic substituents. The cationic substituents and hydrophobic substituent(s) are selected to give a CLogP value of 6.5 or greater, 7.5 or great or even 10 or greater. In order to achieve the desired CLogP value, greater hydrophobicity in the hydrophobic substituent is needed when cationic substituents with less hydrophobicity are used.

The high CLogP value allows the compounds to be non-covalently bonded to polymers that have hydrophobic moieties. For example, the hydrophobic compounds described herein can be non-covalently bonded to a hydrogel materials. The hydrophobic bonding allows for ceragenin compounds to associate with the polymer while having minimal impact on the ability to kill microbes.

Surprisingly and unexpectedly, it has been found that by non-covalently bonding the ceragenin to a polymeric material using hydrophobic/hydrophilic interactions, the hydrophobic ceragenin compound can selectively release from the polymer in the presence of microbes, thereby having a killing affect at lower concentration than one would predict and over an extended period of time. This is in contrast to studies done with covalently bonded ceragenins where immobilization impeded kill rates beyond the initial exposure. The ability of the hydrophobic ceragenin compounds to selectively release from a polymer to kill microbes is highly desirable and a surprising and unexpected result.

In addition, it has been found that the ceragenins as used in the present invention surprisingly kill harmful microbes preferentially over normal flora, which means that the ceragenins can be used at lower concentrations compared to other antimicrobials while achieving the same or better effectiveness. This feature avoids many of the deleterious effects of prior art antimicrobials, many of which tend to kill the "good microbes."

The hydrophobic ceragenin compounds can be incorporated into or formed into medical devices such as medical devices to be implanted into a human or other animal. For example, the hydrogels can be coated on a medical device or incorporated into a polymeric product such as an ophthalmic product. The medical devices incorporating the hydrophobic compounds can controllably release ceragenin compound in a concentration sufficient to meet regulatory requirements for maximum bacterial loads over weeks or even months.

These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION

I. Hydrophobic Ceragenins

Figure 1A:
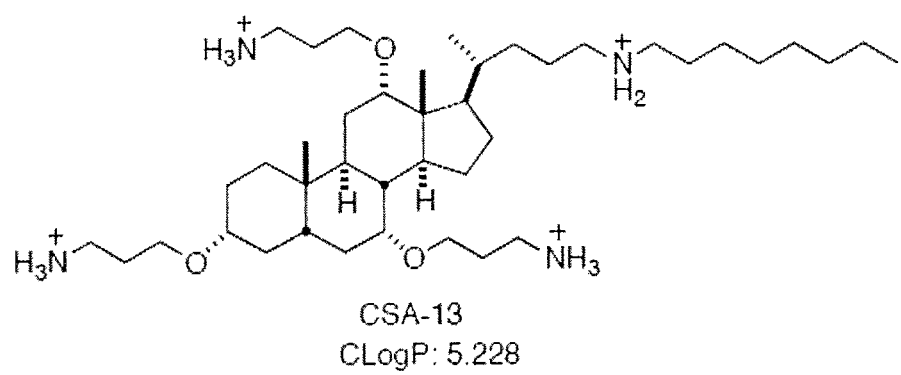
FIG. 1A illustrates example ceragenin compounds with a ClogP value less than 6.3.
Figure 1A:
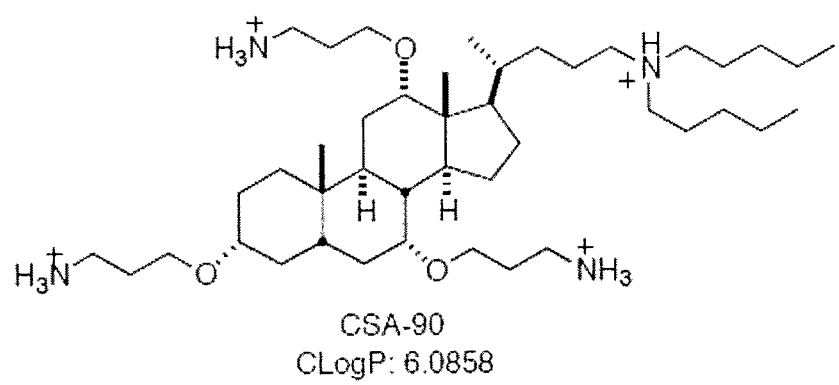
Figure 1A:
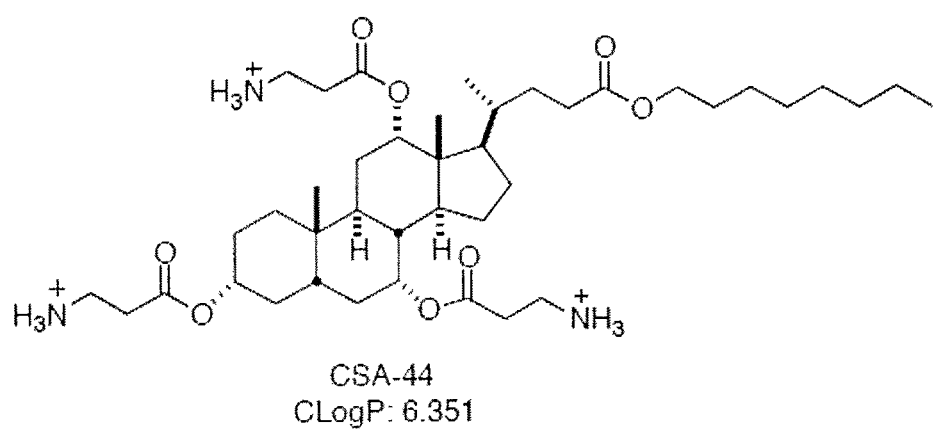

In one embodiment, hydrophobic ceragenin compounds disclosed herein have (i) a sterol structure comprising four fused carbon rings; (ii) at least one cationic substituent attached to each of at least three of the four fused carbon rings so as to form an amphiphilic compound having a hydrophobic sterol face and a hydrophilic cationic face; (iii) at least one hydrophobic substituent attached to at least one of the fused carbon rings; and (iv) wherein the CSA compound has a CLogP value of at least 6.5.

The CLogP value is achieved by selecting a proper hydrophobic substituent(s) in combination with proper cationic substituents. The cationic substituents and hydrophobic substituent(s) are selected to give a CLogP value of 6.5 or greater, 7.5 or great or even 10 or greater.

The ceragenin compound may have a structure as shown in Formula I:

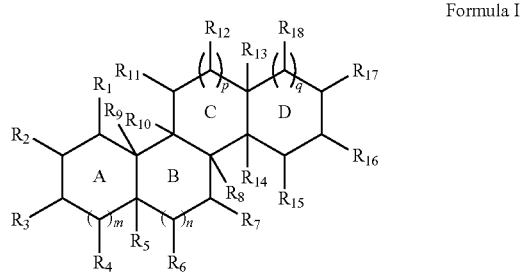

Formula I where rings A, B, C, and D form a fused ring system and at least one of the R groups on 2 or 3 of the 4 four fused rings has a cationic substituent. The other R groups on FIG. I can have a variety of different functionalities, thus providing the ceragenin compound with the desired hydrophobic properties.

In a preferred embodiment, p=1 and q=0 and at least $R_3$, $R_7$, and $R_{12}$ independently include a cationic substituent attached to the fused ring system and $R_{17}$ is a hydrophobic substituent that includes a hydrophobic group selected to give the ceragenin compound its desired hydrophobic/hydrophilic characteristics, which allows the ceragenin compound to non-covalently bond to a polymer and elute out over time and/or be selectively exposed to microbes. The $R_{17}$ substituent may be hydrophobic but still include one or more heteroatoms (O or N) by having sufficient number of carbon atoms attached thereto to form a hydrophobic group. The hydrophobic group may be branched, substituted, or unsubstituted and the branching may occur at the heteroatom (e.g., dialkyl amines). The hydrophobic substituent is preferably attached at $R_{17}$ when q=0 and $R_{18}$ when q=1, but may be attached at other locations on the D ring or on R groups at locations on rings A, B, or C of Formula I. Where a hydrophobic substituent has a hydrophobic group attached to a heteroatom of an alkyl group, the hydrophobic group may have from 1-20 carbons, preferably 8, 9, 10, 11, 12, or more carbons and 20, 18, 16 or fewer carbons or within a range thereof. The hydrophobic group may also include a hydrophobic moiety such as trimethylsilane. The hydrophobic group may include one or more alkyl groups each having 4 or more, 6 or more, 8 or more, 10 or more or 12 or more carbons. The hydrophobic group can be attached to the sterol structure by an alkyl group linking to the heteroatom. The linkage may be an ester, an ether, an amine, or an amide. Ester linkages are preferred where hydrolysis is desired and/or no charge is desired to impart greater hydrophobicity. There the heteroatom includes an amine, the hydrophobic group is preferably a dialkyl. Examples of a suitable hydrophobic substituents having a hydrophobic group as described herein are C13-alkyl amino-C5-alkyl and di-(C1-C20) alkyl amino-(C1-C10)-alkyl, which can be covalently bonded to the D ring at R17 or R18 (Formula I).

Figure 1B:
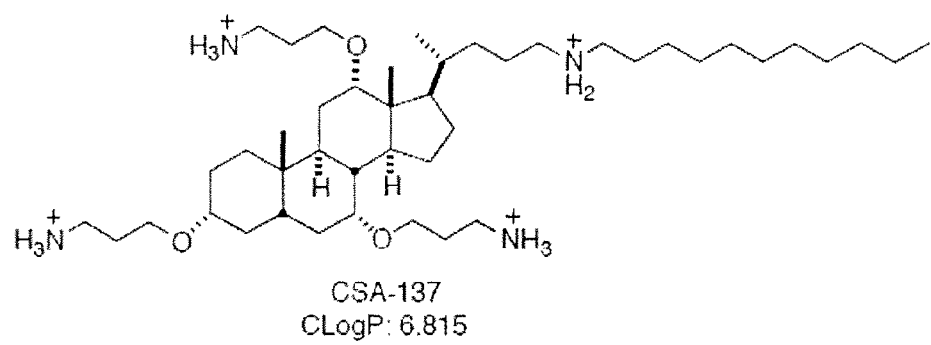
FIG. 1B illustrates example ceragenin compounds with a ClogP value greater than 6.5.
Figure 1B:
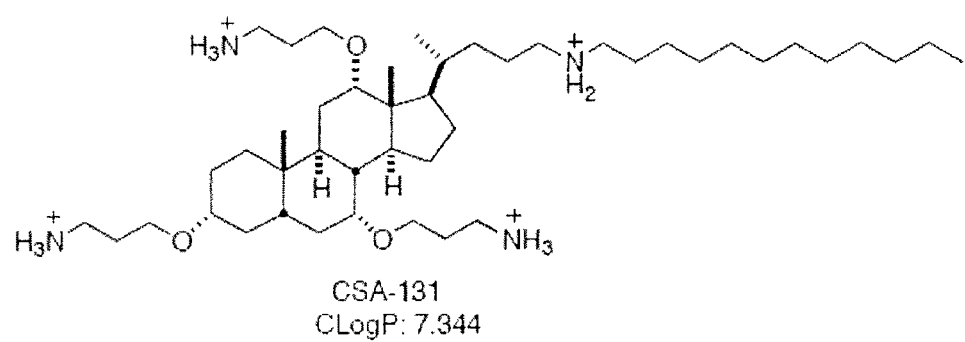
Figure 1B:
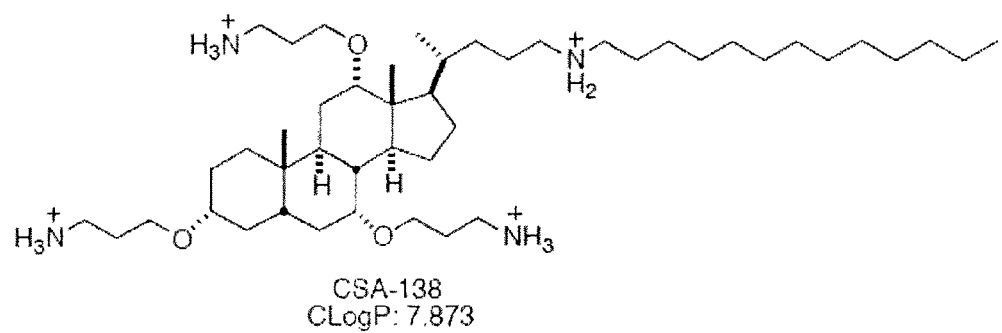

A number of examples of compounds of Formula I that may be used in the embodiments described herein are illustrated in FIG. 1B. Suitable examples of hydrophobic ceragenins useful in producing a composition that will selectively elute from a polymer include, but are not limited to, CSA-131, CSA-132, CSA-133, CSA-134, CSA-135, CSA-137, CSA-138. CSA-144, and CSA-145. The foregoing compounds have a CLogP value greater than 6.5, 7.5, 8.5 and in some cases greater than 10. FIG. 1A illustrates compounds that have a CLogP value less than 6.5. When contrasted with the compounds of FIG. 1B, the compounds of FIG. 1A illustrate the types of changes that impart the desired hydrophobicity of a CLogP value greater than 6.5, 7.5, 8.5, or 10. For example, where the heteroatom is part of an ester group, a hydrocarbon chain length of 9 or greater is sufficient to impart the desired hydrophobicity. Where an amine group is the heteroatom, 11 carbon atoms are more is sufficient. Other moieties such as trimethyl silane can be added to allow for amine groups to be used with shorter chain lengths or to provide additional hydrophobicity.

With reference again to Formula I, more specifically, each of fused rings A, B, C, and D is independently saturated, or is fully or partially unsaturated, provided that at least two of A, B, C, and D are saturated, wherein rings A, B, C, and D form a ring system; each of m, n, p, and q is independently 0 or 1; each of $R_1$ through $R_4$, $R_6$, $R_7$, $R_{11}$, $R_{12}$, $R_{15}$, and $R_{16}$ is independently selected from the group consisting of hydrogen, hydroxyl, a substituted or unsubstituted ($C_1$-$C_{10}$) alkyl, ($C_1$-$C_{10}$) hydroxyalkyl, ($C_1$-$C_{10}$) alkyloxy-($C_1$-$C_{10}$) alkyl, ($C_1$-$C_{10}$) alkylcarboxy-($C_1$-$C_{10}$) alkyl, ($C_1$-$C_{10}$) alkylamino-($C_1$-$C_{10}$)alkyl, ($C_1$-$C_{10}$) alkylamino-($C_1$-$C_{10}$) alkylamino, ($C_1$-$C_{10}$) alkylamino-($C_1$-$C_{10}$) alkylamino-($C_1$-$C_{10}$) alkylamino, a substituted or unsubstituted ($C_1$-$C_{10}$) aminoalkyl, a substituted or unsubstituted aryl, a substituted or unsubstituted arylamino-($C_1$-$C_{10}$) alkyl, ($C_1$-$C_{10}$) haloalkyl, $C_2$-$C_6$ alkenyl, $C_2$-$C_6$ alkynyl, oxo, a linking group attached to a second steroid, a substituted or unsubstituted ($C_1$-$C_{10}$) aminoalkyloxy, a substituted or unsubstituted ($C_1$-$C_{10}$) aminoalkyloxy-($C_1$-$C_{10}$) alkyl, a substituted or unsubstituted ($C_1$-$C_{10}$) aminoalkylcarboxy, a substituted or unsubstituted ($C_1$-$C_{10}$) aminoalkylaminocarbonyl, a substituted or unsubstituted ($C_1$-$C_{10}$) aminoalkylcarboxamido, $H_2N$—HC($Q_5$)-C(0)-0-, $H_2N$—HC($Q_5$)-C(0)-N(H)—, ($C_1$-$C_{10}$) azidoalkyloxy, ($C_1$-$C_{10}$) cyanoalkyloxy, P.G.-HN—HC ($Q_5$)-C(0)-0-, ($C_1$-$C_{10}$) guanidinoalkyloxy, ($C_1$-$C_{10}$) quaternaryammoniumalkylcarboxy, and ($C_1$-$C_{10}$) guanidinoalkyl carboxy, where $Q_5$ is a side chain of any amino acid (including a side chain of glycine, i.e., H), P.G. is an amino protecting group, and each of $R_5$, $R_8$, $R_9$, $R_{10}$, $R_{13}$, and $R_{14}$ is independently deleted when one of fused rings A, B, C, or D is unsaturated so as to complete the valency of the carbon atom at that site, or selected from the group consisting of hydrogen, hydroxyl, a substituted or unsubstituted ($C_1$-$C_{10}$) alkyl, ($C_1$-$C_{10}$) hydroxyalkyl, ($C_1$-$C_{10}$) alkyloxy-($C_1$-$C_{10}$) alkyl, a substituted or unsubstituted ($C_1$-$C_{10}$) aminoalkyl, a substituted or unsubstituted aryl, ($C_1$-$C_{10}$) haloalkyl, $C_2$-$C_6$ alkenyl, $C_2$-$C_6$ alkynyl, oxo, a linking group attached to a second steroid, a substituted or unsubstituted ($C_1$-$C_{10}$) aminoalkyloxy, a substituted or unsubstituted ($C_1$-$C_{10}$) aminoalkylcarboxy, a substituted or unsubstituted ($C_1$-$C_{10}$) aminoalkylaminocarbonyl, $H_2N$—HC($Q_5$)-C(0)-0-, $H_2N$—HC($Q_5$)-C(0)-N(H)—, ($C_1$-$C_{10}$) azidoalkyloxy, ($C_1$-$C_{10}$) cyanoalkyloxy, P.G.-HN—HC ($Q_5$)-C(0)-0-, ($C_1$-$C_{10}$) guanidinoalkyloxy, and ($C_1$-$C_{10}$) guanidinoalkylcarboxy, where Q5 is a side chain of any amino acid, PG. is an amino protecting group, provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of a substituted or unsubstituted ($C_1$-$C_{10}$) aminoalkyl, a substituted or unsubstituted ($C_1$-$C_{10}$) aminoalkyloxy, ($C_1$-$C_{10}$) alkylcarboxy-($C_1$-$C_{10}$) alkyl, ($C_1$-$C_{10}$) alkylamino-($C_1$-$C_{10}$) alkylamino, ($C_1$-$C_{10}$) alkylamino-($C_1$-$C_{10}$) alkylamino ($C_1$-$C_{10}$) alkylamino, a substituted or unsubstituted ($C_1$-$C_{10}$) aminoalkylcarboxy, a substituted or unsubstituted arylamino ($C_1$-$C_{10}$) alkyl, a substituted or unsubstituted ($C_1$-$C_{10}$) aminoalkyloxy ($C_1$-$C_{10}$) aminoalkylaminocarbonyl, a substituted or unsubstituted ($C_1$-$C_{10}$) aminoalkylaminocarbonyl, a substituted or unsubstituted ($C_1$-$C_{10}$) aminoalkylcarboxyamido, a ($C_1$-$C_{10}$) quaternaryammonium alkylcarboxy, $H_2N$—HC($Q_5$)-C(0)-0-, $H_2N$—HC($Q_5$)-C(0)-N(H)—, ($C_1$-$C_{10}$) azidoalkyloxy, ($C_1$-$C_{10}$) cyanoalkyloxy, P.G.-HN—HC (Q5)-C(0)-O—, ($C_1$-$C_{10}$) guanidinoalkyloxy, and a ($C_1$-$C_{10}$) guanidinoalkylcarboxy; or a pharmaceutically acceptable salt thereof. Additional examples of specific CSA compounds are disclosed in Applicant's copending U.S. application Ser. No. 13/288,902 Filed Nov. 3, 2012, which is incorporated herein by reference.

A "ring" as used herein can be heterocyclic or carbocyclic. The term "saturated" used herein refers to the fused ring of Formula I having each atom in the fused ring either hydrogenated or substituted such that the valency of each atom is filled. The term "unsaturated" used herein refers to the fused ring of Formula I where the valency of each atom of the fused ring may not be filled with hydrogen or other substituents. For example, adjacent carbon atoms in the fused ring can be doubly bound to each other. Unsaturation can also include deleting at least one of the following pairs and completing the valency of the ring carbon atoms at these deleted positions with a double bond; such as $R_5$ and $R_9$; $R_8$ and $R_{10}$; and $R_{13}$ and $R_{14}$.

The term "unsubstituted" used herein refers to a moiety having each atom hydrogenated such that the valency of each atom is filled.

The term "halo" used herein refers to a halogen atom such as fluorine, chlorine, bromine, or iodine.

Examples of amino acid side chains include but are not limited to H (glycine), methyl (alanine), —$CH_2$—(C=0)-$NH_2$ (asparagine), —$CH_2$—SH (cysteine), and —CH(OH)—$CH_3$ (threonine).

An alkyl group is a branched or unbranched hydrocarbon that may be substituted or unsubstituted. Examples of branched alkyl groups include isopropyl, sec-butyl, isobutyl, tert-butyl, sec-pentyl, isopentyl, tert-pentyl, isohexyl. Substituted alkyl groups may have one, two, three or more substituents, which may be the same or different, each replacing a hydrogen atom. Substituents are halogen (e.g., F, Cl, Br, and I), hydroxyl, protected hydroxyl, amino, protected amino, carboxy, protected carboxy, cyan, methylsulfonylamino, alkoxy, acyloxy, nitro, and lower haloalkyl.

The term "substituted" used herein refers to moieties having one, two, three or more substituents, which may be the same or different, each replacing a hydrogen atom. Examples of substituents include but are not limited to halogen (e.g., F, Cl, Br, and I), hydroxyl, protected hydroxyl, amino, protected amino, carboxy, protected carboxy, cyan, methylsulfonylamino, alkoxy, alkyl, aryl, aralkyl, acyloxy, nitro, and lower haloalkyl.

An aryl group is a $C_{6\_20}$ aromatic ring, wherein the ring is made of carbon atoms (e.g., $C_6$-$C_{14}$, $C_{6\_10}$ aryl groups). Examples of haloalkyl include fluoromethyl, dichloromethyl, trifluoromethyl, 1,1-difluoroethyl, and 2,2-dibromoethyl.

An aralkyl group is a group containing 6-20 carbon atoms that has at least one aryl ring and at least one alkyl or alkylene chain connected to that ring. An example of an aralkyl group is a benzyl group.

A linking group is any divalent moiety used to link one compound to another. For example, a linking group may link a second compound to a compound of Formula I. An example of a linking group is ($C_1$-$C_{10}$) alkyloxy-($C_1$-$C_{10}$) alkyl.

Amino-protecting groups are known to those skilled in the art. In general, the species of protecting group is not critical, provided that it is stable to the conditions of any subsequent reaction(s) on other positions of the compound and can be removed at the appropriate point without adversely affecting the remainder of the molecule. In addition, a protecting group may be substituted for another after substantive synthetic transformations are complete. Clearly, where a compound differs from a compound disclosed herein only in that one or more protecting groups of the disclosed compound has been substituted with a different protecting group, that compound is within the disclosure. Further examples and conditions are found in T. W. Greene, Protective Groups in Organic Chemistry, (1st ed., 1981, 2nd ed., 1991).

A person of skill will recognize that various ceragenin compounds described herein preserve certain stereochemical and electronic characteristics found in steroids. The term "single face," as used herein, refers to substituents on the fused sterol backbone having the same stereochemical orientation such that they project from one side of the molecule. For example, substituents bound at $R_3$, $R_7$ and $R_{12}$ of Formula I may be all 13-substituted or a-substituted. The configuration of the moieties $R_3$, $R_7$ and $R_{12}$ may be important for interaction with the cellular membrane.

Compounds include but are not limited to compounds having cationic substituents (e.g., amine or guanidine groups) covalently attached to a sterol backbone or scaffold at any carbon position, e.g., cholic acid. In various embodiments, a group is covalently attached at anyone, or more, of positions $R_3$, $R_7$, and $R_{12}$ of the sterol backbone. In additional embodiments, a group is absent from anyone, or more, of positions $R_3$, $R_7$, and $R_{12}$ of the sterol backbone.

Other ring systems can also be used, e.g., 5-member fused rings. Compounds with backbones having a combination of 5- and 6-membered rings are also contemplated. Cationic functional groups (e.g., amine or guanidine groups) can be separated from the backbone by at least one, two, three, four or more atoms.

Ceragenins with hydrophobic substituents can be prepared using the techniques described in Applicant's U.S. Pat. No. 6,767,904, with the modification being using longer chain alkyls to form a more hydrophobic substituent. For example, instead of using an octyl amine to form the functional group at $R_{17}$, a corresponding longer chain amine can be used.

II. Non-Covalent Incorporation of Ceragenins into a Polymer

Hydrophobic ceragenin compounds incorporated into a polymer can be non-covalently associated with the polymer. Upon contact with moisture, the ceragenin can leach or elute from the polymer. Ceragenins are generally soluble in water, and ceragenins can be associated with polymers to control release rates. Selection of appropriate polymer and ceragenin structures allows for an extended period of release of the ceragenin.

For example, the chain extending from a heteroatom (e.g., N) on $R_{17}$ (Formula I) can be tailored to allow varied rates of elution from a hydrogel polymer. Exemplary chains included, lipids, hydrophobic chains (e.g., aliphatic), hydrophilic (e.g., polyethyleneoxide), or any chain that interacts with the polymer is a way that allows modification of the rate of elution. Longer chain lengths will retain the ceragenin within the polymer matrix (in particular the hydrophobic domains). In one embodiment, the ceragenin compound may have a carbon chain of at least 9 carbons attached to the D ring of the sterol group (Formula I). For example, the carbon chain of at least 9 carbons may be attached to $R_{17}$ group of Formula I, or the $C_{24}$ carbon or other similar carbon of a sterol backbone.

The particular ceragenins incorporated into the polymer may be soluble or partially soluble in aqueous solutions. Additionally, ceragenins when blended with the water and the appropriate surfactant can be handled in the form of gels, or emulsions. Block copolymers based on ethylene oxide and/or propylene oxide, in particular, Pluronic-type surfactants, are especially useful for this purpose. Pluronic is a product of BASF, a business with offices in Port Arthur, Tex., USA.

Ceragenin compounds can be incorporated into a polymer at any suitable step during manufacture of a hydrogel material or product. For example, in an embodiment, a polymer can be brought into contact with a solution of ceragenins by immersion, spraying, printing, or coating, etc. Suitable solvents include short chain alcohols such as ethanol, methanol, isopropyl alcohol, and the like. If desired, the solvent used to incorporate the ceragenin can be removed, for example, by evaporation. If necessary the polymer can be dried by utilizing forced hot air, oven drying, air at room temperature, microwave drying, or the use of heated drying drums, vacuum chambers, etc. In some manufacturing systems the normal air flow and temperature sufficiently dry the substrate without a discrete drying process.

Ceragenin compounds are known to be soluble in water. Alternatively, ceragenin compounds are also soluble in such materials as ethanol (and other alcohols), propylene glycol, glycerine, and polyols, or mixtures thereof with or without water can be used in incorporate ceragenin compounds into a polymeric material. Furthermore ceragenins can be incorporated as gels, emulsions, suspensions, and in dry form.

In another embodiment ceragenin is incorporated into a polymer during polymerization of the monomers. In these processes, the ceragenin can be included in the monomer blend during polymerization. The ceragenin in final polymer can be noncovalently incorporated into the polymer and will accordingly elute when contacted with a solvent such as water.

III. Elution

When the ceragenin compound is incorporated into a polymeric material, the hydrophobicity/hydrophilicity of the polymer and the ceragenin compound are selected to cause the ceragenin compound to non-covalently bond to the hydrogel polymer. The non-covalent bonding prevents the ceragenin compound from being released all at once in the presence of a solvent. Rather, the bonding allows the ceragenin compound to be released over time in the presence of a solvent.

The non-covalent bonding depends on the composition of both the polymer and the ceragenin and therefore need to be selected together to produce the desired elution. The selection is typically carried out by selecting a particular polymer having desired chemical and mechanical properties for a particular application. For example, if the polymer is coated on a medical device to be implanted in vascular tissue, the polymer is selected for compatibility with vascular tissue and blood. If the polymer is used to form a contact lens, the polymer is selected for its compatibility with the eye and the need to form the polymer in a shape that will correct vision. The hydrophobicity/hydrophilicity of the polymer material is therefore somewhat constrained by the particular application.

The ceragenin compound has a hydrophobicity selected to provide non-covalent bonding to the particular polymer. The ceragenin may be selected to have R groups that bond non-covalently the functional groups of the polymer. For example, a polyacrylate based polymer may have a certain percentage of hydrophobic groups and hydrophilic groups in the polymer matrix and the ceragenin compound may be selected to have a hydrophobic $R_{17}$ substituent (where q=0 in Formula I) that non-covalently bonds to the hydrophobic groups of the polymer to cause a relatively consistent elution over a period of days or weeks.

In some cases, the solvent may also influence elution. In one embodiment, the solvent is water. In some embodiments, the solvent may be saline.

In one embodiment, the hydrogel polymer and the ceragenin compound are selected to yield non-covalent bonding that provides a release rate of 0.1-100 µg/ml, 0.5-50 µg/ml, or 1-10 µg/ml at three days, one week, or one month in water or saline. In one embodiment, the foregoing elution rate remains within the foregoing ranges for at least 3 days, one week, or one month. These elution rates are achieved in part by the non-covalent bonding that prevents rapid release of the compound, which results in more compound being available at a later date.

As mentioned above, it has been surprisingly found that non-covalently bound ceragenins in hydrogels selectively elute in the presence of microbes. This is a surprising and unexpected result that makes the use of polymer-ceragenin compounds particularly advantageous as compared to other materials, such as ceragenins covalently bonded to the surface of a polymer.

Those skilled in the art will recognize that the selection of the particular polymer and ceragenin compound will depend on the particular application and the appropriate selection can be made by one of skill in the art using the teachings and examples provided herein.

IV. Hydrogel Polymers

One type of polymer that is particularly useful for incorporating hydrophobic ceragenin compounds are hydrogel polymers.

Examples of suitable hydrogel polymers include, but are not limited to, polyvinyl alcohol, sodium polyacrylate, acrylate polymers, polyethylene oxide, poly(2-acrylamido-2-methyl-1-prop anesulfonic acid) (polyAMP S), polyvinylpyrrolidone, polyacrylamide, silicone, agarose, methylcellulose, hyaluronan, hydrolyzed polyacrylicnitrile, combinations of these. The hydrogels may be copolymers. The copolymers may include hydrophobic and hydrophilic units.

In one embodiment, the hydrogel is suitable for manufacturing a contact lens. Hydrophilic contact lenses can be formed from cross-linked polymers based on hydrophilic derivatives of acrylic or methacrylic acid, hydrophilic vinylic monomers such as vinylpyrrolidone, and the like. The hydrogels preferably include hydrophobic regions made from blocks or monomers that are hydrophobic.

An example of a suitable contact lens hydrogel is disclosed in U.S. Pat. No. 8,011,784, which is incorporated herein by reference.

The hydrogel polymers may be formed into a contact lens having a shape and structure suitable for correcting vision. Those skilled in the art are familiar with the shapes and structures of hydrogel polymers that can provide correction for vision. Other devices that can be formed from the hydrogels include wound healing devices such as tissue scaffolds and wound dressing.

V. Medical Devices and Coatings

Figure 2:
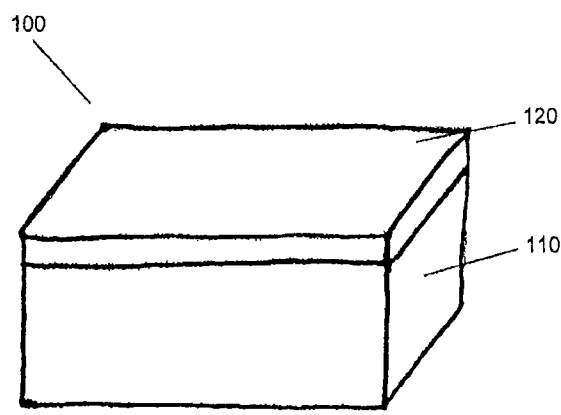
FIG. 2 is a schematic representation of a substrate with a polymeric coating.

The polymers described herein may be used in various applications, including, but not limited to, medical devices, coatings, bandages, implants, tissue scaffolding, and the like. FIG. 2 is a schematic representation of a medical device 100 that includes a substrate 110 and a polymeric coating 120.

The substrate 110 may be made of any material suitable for supporting and/or adhering to a hydrogel material. The substrate can be polymeric, metallic, an alloy, inorganic, and/or organic. In one embodiment, the substrate is a biocompatible or bioabsorbable material. Suitable biocompatible metallic materials include, but are not limited to, stainless steel, tantalum, titanium alloys (including nitinol), and cobalt alloys (including cobalt-chromium-nickel alloys). Suitable nonmetallic biocompatible materials include, but are not limited to, polyamides, polyolefins (i.e. polypropylene, polyethylene etc.), nonabsorbable polyesters (i.e. polyethylene terephthalate), and bioabsorbable aliphatic polyesters (i.e. homopolymers and copolymers of lactic acid, glycolic acid, lactide, glycolide, para-dioxanone, trimethylene carbonate, $\epsilon$-caprolactone, and the like, and combinations of these)

The thickness of the substrate will depend on the device and the material but may be 0.1, 1.0, 10 mm or greater and/or 100, 10, or 1 mm or less and/or within a range thereof.

The thickness of polymeric coating 120 is generally less than the thickness of substrate 110. Polymeric coating 120 may have a thickness of 0.01, 0.1, 1.0, or 10 mm or greater and 100, 10, 1.0, or 0.1 mm or less or within a range thereof.

The polymeric coating 120 can be continuous or non-continuous. The coating may be applied to the substrate using techniques such as dip coating, spin coating, or the like.

Examples of medical devices that can be formed from a polymer containing hydrophobic ceragenin compounds or can have such a polymer coated thereon include but are not limited to bone implants, bone pins, bone screws, tissue grafts, airway devices such as endotracheal tubes, implantable devices such as coronary stents, peripheral stents, catheters, arterio-venous grafts, by-pass grafts, pacemaker and defibrillator leads, anastomotic clips, arterial closure devices, patent foramen ovale closure devices, and drug delivery balloons. The polymer may be coated on or form any portion of the structures of such devices and is preferably on an outer surface and more preferably on an out service that contacts tissue or a tissue air interface (when the device is implanted).

VI. Stabilization of Ceragenins by pH

In one embodiment a ceragenin compound can have hydrolysable linkages that attach the cationic substituents to the sterol group (e.g., ester bonds). Hydrolysis of these linkages inactivates the ceragenin. To make the ceragenin stable, an acid can be added to achieve a pH less than 6, 5.5, 5, or 4.5 and optionally greater than 2, 2.5, or 3 or a range thereof. Stability before use is important to give a desired shelf life and instability during and after use can be desirable to prevent long term accumulation of ceragenins in biological systems.

It may be advantageous to adjust the degree of neutralization of the polymer to improve the stability of the ceragenin. The degree of neutralization of the polymer can be adjusted during its manufacturing process, or subsequently. Alternatively, the ceragenin can be suspended or dissolved in an acidic solution; and when the ceragenin suspension or solution is added to the hydrogel polymer the degree of neutralization of the hydrogel would thereby be adjusted.

VII. Examples

To better understand the mechanism by which hydrophobic ceragenin compounds can prevent bacterial colonization, the bonding between CSA-138 and a hydrogel used in contact lenses was evaluated. In a first example, we determined the rate at which CSA-138 elutes from a hydrogel suitable for use in contact lenses. To quantify the amount of ceragenin eluting from the hydrogel, we used LC/MS using a mass-labeled internal standard. However, this method only gave detection limits of about 2 µg/ml, and we were able to effectively kill bacteria at constant elution rates below the detection limit. For example, the elution fell below detection limits within five days of elution from lenses in which CSA-138 had been incorporated at 1%, yet the ceragenins appeared to still be providing suitable kill rates.

To decrease the detection limit for CSA-138, we prepared a radiolabeled version of CSA-138 (CSA-138T2), incorporated it into contact lenses, and quantified its elution elution from lenses using scintillation counting.

Example 1

Lenses containing 1% CSA-138 were stored in 0.5 mL phosphate buffered saline (PBS) prior to testing. One set of lenses was autoclaved for 45 min before elution studies were performed. For elution studies, lenses were suspended in 2 ml aliquots of PBS, 10% TSB growth medium, 10% TSB growth medium containing $10^6$ CFU of *Staphylococcus aureus*, or 10% TSB growth medium containing $10^6$ CFU of *Pseudomonas aeruginosa*. Corresponding aliquots were exchanged every 24 h, including bacterial inocula. Samples were removed every 24 h and analyzed for the presence of CSA- 138 using scintillation counting. A standard curve was generated to correlate counts per minute to concentration of CSA-138. All experiments were performed in triplicate.

Figure 3:
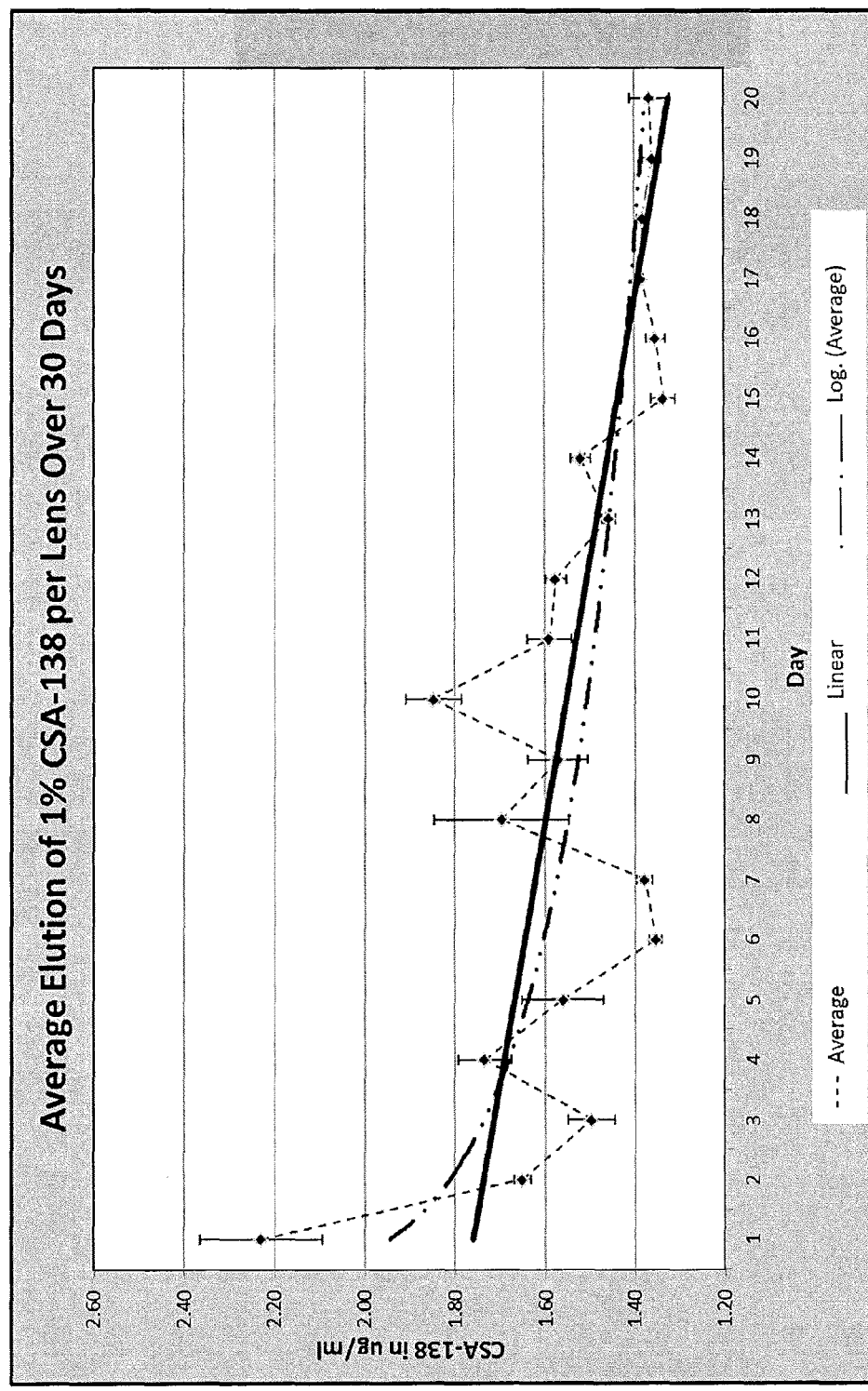
FIG. 3 is a graph showing elution of a ceragenin from a hydrogel in phosphate buffered saline.

Though some variations from day to day were observed, a recognizable trend was observed in the elution profile of lenses suspended in PBS (FIG. 3). As expected, the elution on the first day was relatively high (about 2.2 µg/ml). Over the course of following 19 days, daily elution changed from approximately 1.6 to 1.4 µg/ml per day.

Figure 4:
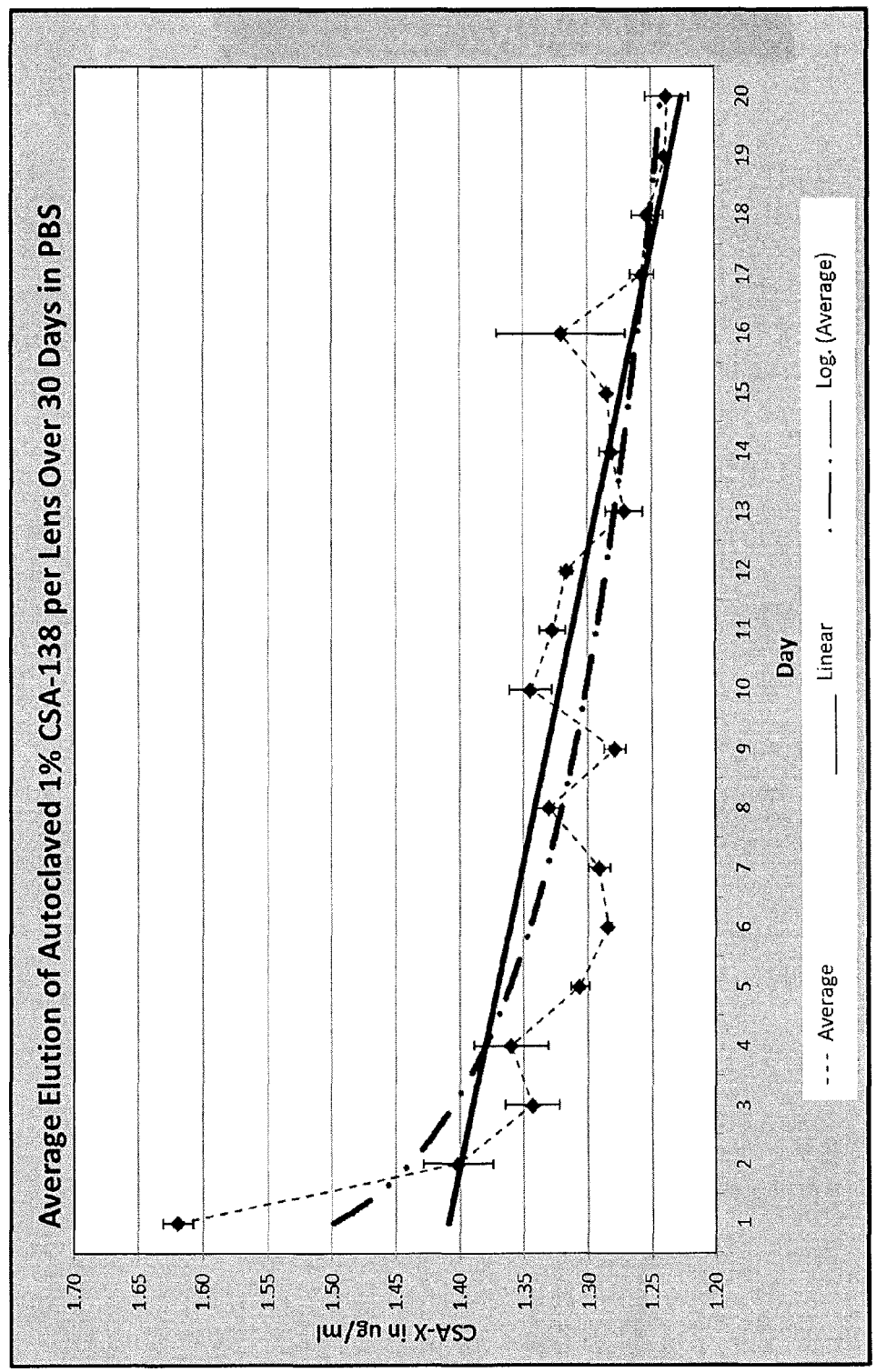
FIG. 4 is a graph showing elution of a ceragenin from a hydrogel following autoclaving.

A comparable elution profile was observed with lenses that were autoclaved prior to the start of the study, except that the initial amount of material that eluted decreased somewhat (FIG. 4). This decrease in elution is likely due to enhanced elution into the storage solution during the autoclaving process. Over the course of the study (from day 2 to 20), the amount of CSA-138 that eluted changed from approximately 1.4 to 1.2 µg/ml per day.

It was anticipated that an increase in the osmolality of an aqueous solution would decrease the solubility of CSA-13 and slow elution. We determined the elution profile in 10% TSB in PBS, and as expected elution decreased (FIG. 5) to match that seen with lenses that had been autoclaved.

Figure 6:
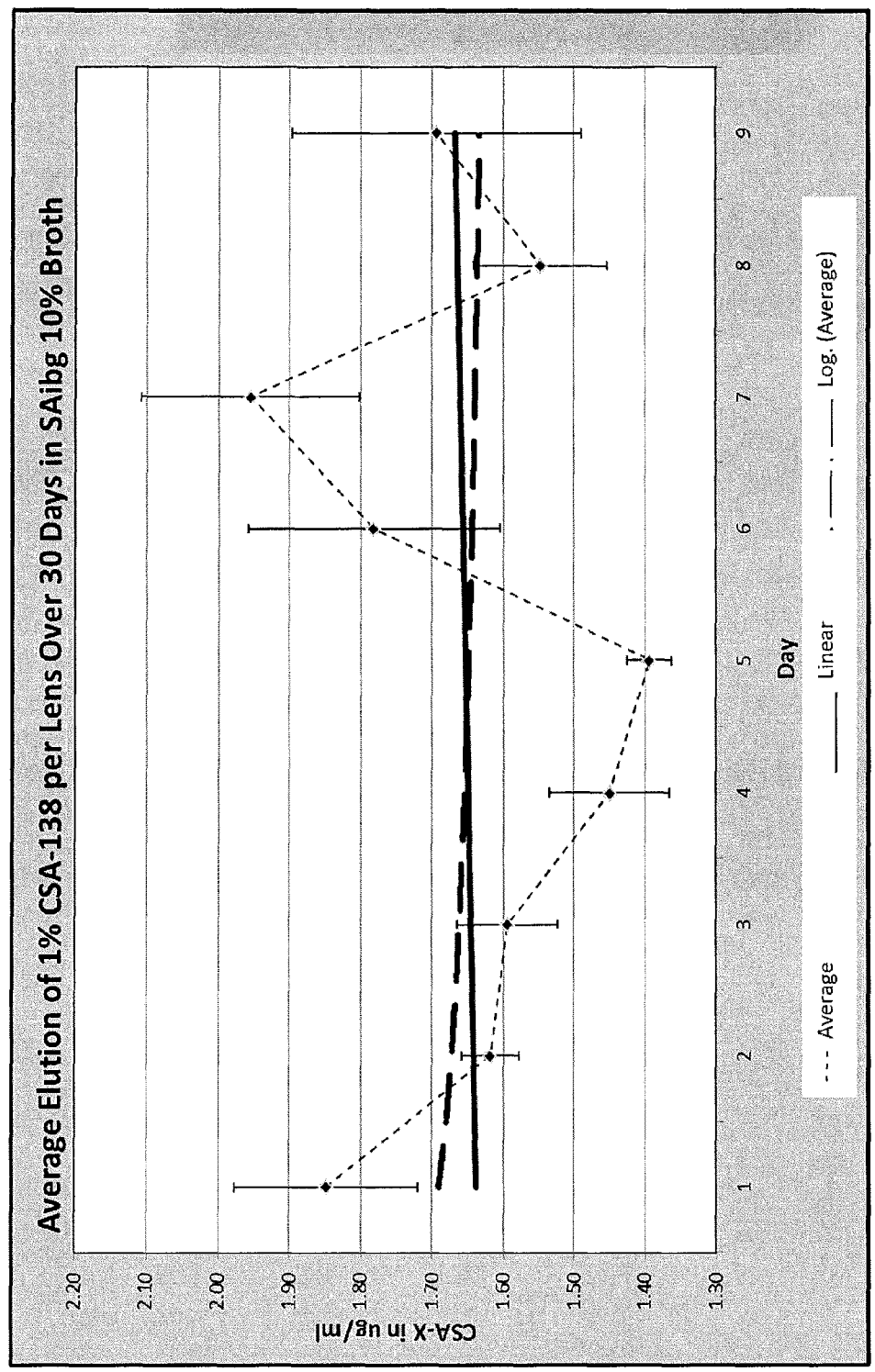
FIG. 6 is a graph showing elution of a ceragenin from a hydrogel in buffer and $10^6$ CFU of *S. aureus*.
Figure 7:
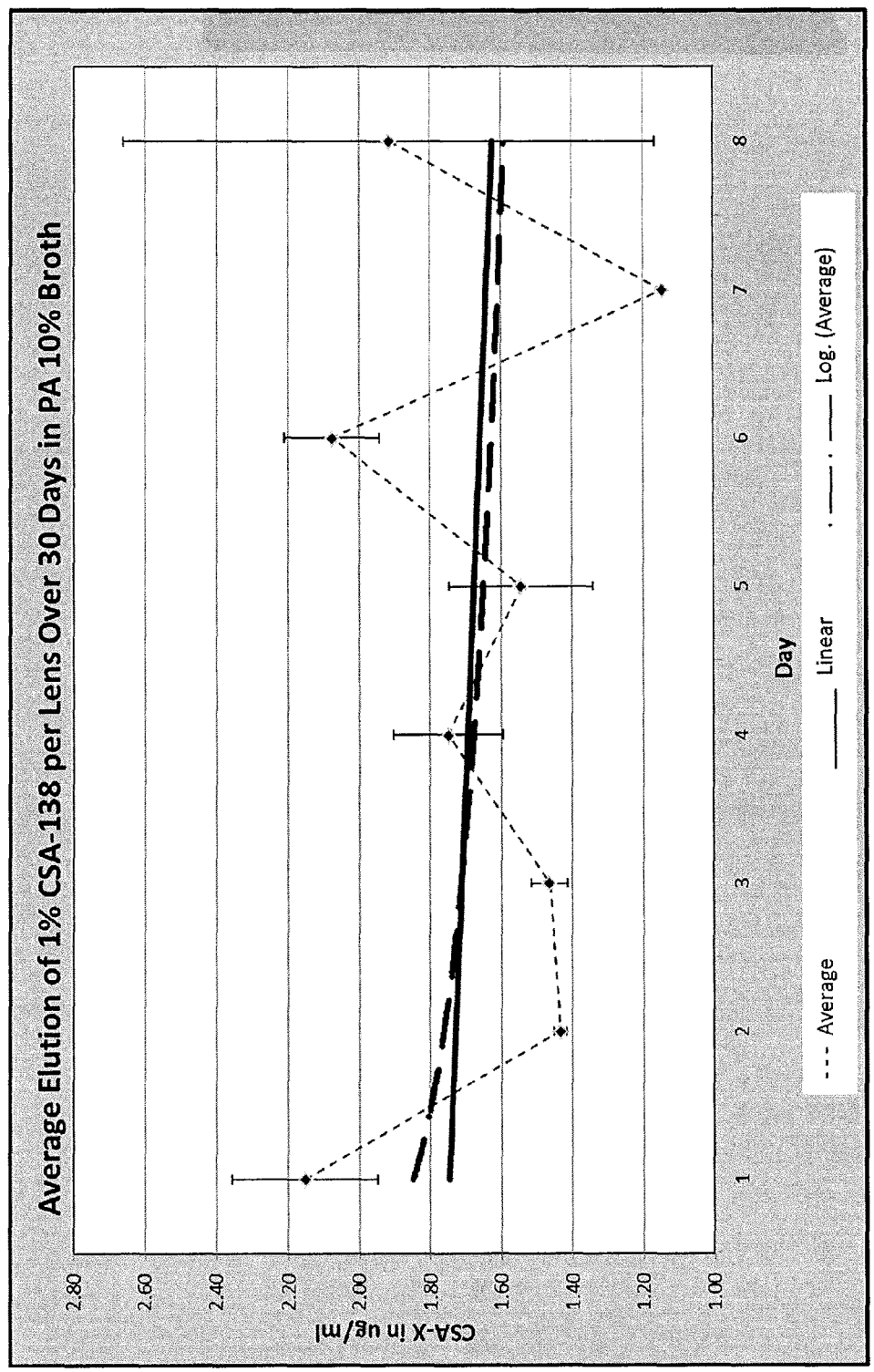
FIG. 7 is a graph showing elution of a ceragenin from a hydrogel in buffer and $10^6$ CFU of *P. aeruginosa*.

Because kill rates appeared to be happening at such low concentrations, we hypothesized that the presence of bacteria was influencing the elution of CSA-138 from lenses. To test this hypothesis, lenses were incubated with *S. aureus* or *P. aeruginosa* and elution was monitored. These experiments were performed for nine and eight days, respectively. Elution of CSA-138 fluctuated substantially and to a much greater extent than outside of the presence of bacteria (FIGS. 6 and 7). Because of these variations, the experiments were shortened relative to elution experiments without bacteria. Though there was substantial variation in the elution in the presence of bacteria, it was possible to determine the significance of the differences in elution comparing samples with and without bacteria. After the first day, differences gave a p value of 0.05 and for many of the days, the p value was below 0.01. These results argue that bacteria impact elution of CSA-138 from lenses.

The MIC values of CSA-138 for *S. aureus* and for *P. aeruginosa* are 0.5 and 1.0 µg/ml, respectively. The elution of CSA-138 from lenses gives concentrations that are just able to eliminate the inocula introduced. Autoclaving the lenses, increasing the osmolality in the surrounding solution, and the presence of bacteria impact the elution profile modestly.

Figure 5:
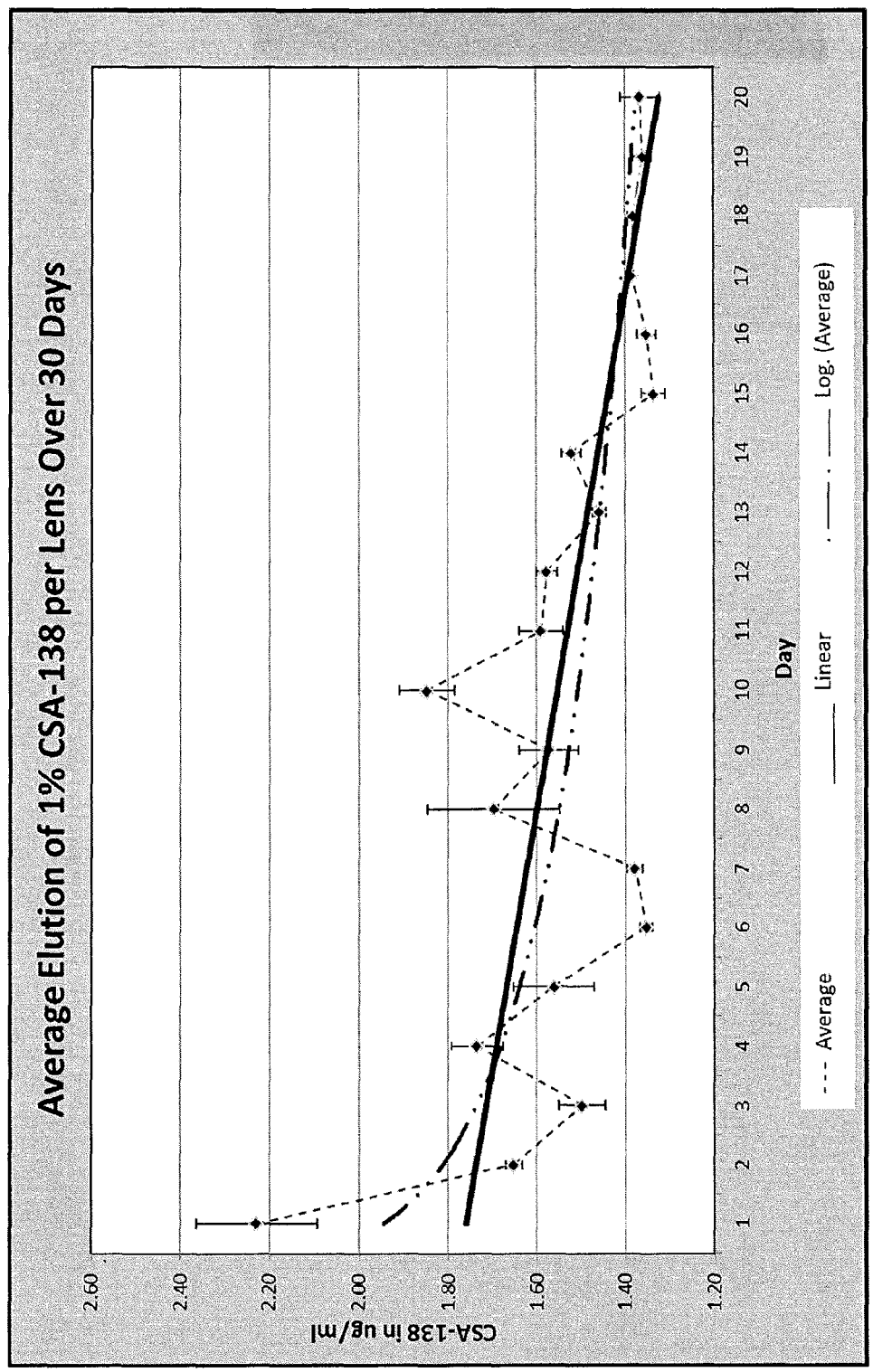
FIG. 5 is a graph showing elution of a ceragenin from a hydrogel in phosphate buffered saline and tryptic soy broth.

If one takes the elution profile given in FIG. 5 and extends the trend until elution of CSA-138 drops below 1 µg/ml, this would require about 40 days (elution decreases from 1.4 to 1.2 µg/ml per day between days two and 20; a decrease from 1.2 to 1.0 µg/ml per day would be expected to require another 19 days). Thus, it would be expected that elution of CSA-138 would be sufficient to eliminate reasonable inocula of bacteria for as many as 40 days. As noted in a previous report, elution of CSA-138 from lenses prevents colonization by *S. aureus* for 30 consecutive days and by *P. aeruginosa* for 19 days. These studies are performed with relatively high inocula ($10^6$ CFU), and it is anticipated that CSA-138 eluting after 30 days would be sufficient to eliminate smaller inocula.

Optimization of the structure of CSA-138 has yielded a potent antimicrobial agent that associates with contact lens material and elutes at the concentration necessary to eliminate substantial inocula of Gram-positive and -negative bacteria. Considering the number of bacteria to which lenses are typically exposed, it is likely that lower concentrations of CSA-138 could be used while continuing to prevent bacterial growth on lenses.

For purposes of this invention, "physiological conditions" are aqueous conditions where the pH, temperature, and salt concentrations are generally suitable for sustaining life (e.g., for many, but not all devices, physiological conditions is often a pH near 7, temperatures near 37° C., and salt concentration near 150 mM).

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A hydrophobic cationic steroidal anti-microbial (CSA) compound comprising:
   a sterol structure comprising four fused carbon rings;
   at least one cationic substituent attached to each of at least three of the four fused carbon rings so as to form an amphiphilic compound having a hydrophobic sterol face and a hydrophilic cationic face;
   at least one hydrophobic substituent attached to at least one of the fused carbon rings;
   wherein the CSA compound has a CLogP value of at least 6.5 and a structure as in Formula (1):

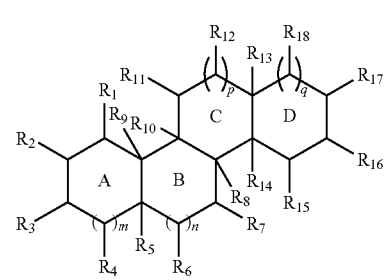

Formula (I)

wherein
   q=0 and p=1;
   $R_3$, $R_7$ and $R_{12}$ independently include a cationic group;
   $R_{17}$ is a hydrophobic substituent selected from a trimethylsilane and a hydrophobic substituent which includes a heteroatom and a hydrocarbon group of at least 9 carbon atoms and fewer than 16 carbon atoms distal to the heteroatom; and
   $R_1$, $R_2$, $R_4$-$R_6$, $R_8$-$R_{16}$ are any substituent, with the proviso that $R_{16}$ does not form a fused ring with $R_{17}$.

2. A hydrophobic CSA compound as in claim 1, wherein the CLogP value is at least 7.5.

3. A hydrophobic CSA compound as in claim 1, wherein the ClogP value is at least 8.5.

4. A hydrophobic CSA compound as in claim 1, wherein the hydrophobic substituent includes a trimethylsilane.

5. A hydrophobic CSA compound as in claim 1, wherein the hydrophobic substituent is attached at the C17 position of the steroid structure.

6. A hydrophobic CSA compound as in claim 1, wherein the hydrophobic substituent includes a heteroatom and a hydrocarbon group of at least 9 carbon atoms and fewer than 16 carbon atoms distal to the heteroatom.

7. A hydrophobic CSA compound as in claim 6, wherein the hydrocarbon group is a straight chain hydrocarbon.

8. A hydrophobic CSA compound as in claim 7, wherein the hydrocarbon group includes from 11 to 15 carbon atoms.

9. A hydrophobic CSA as in claim 1, wherein the CSA compound is selected from the group consisting of:
CSA-131
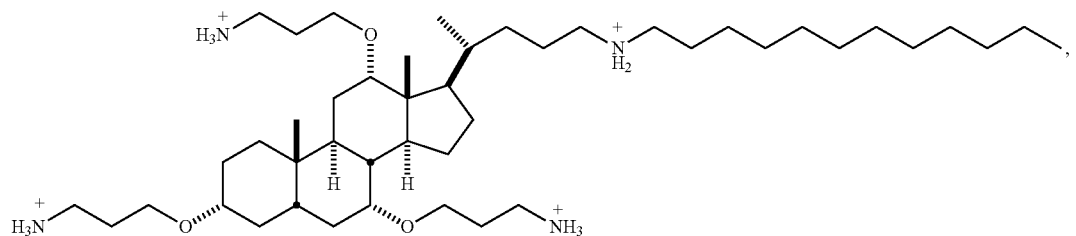
CSA-134
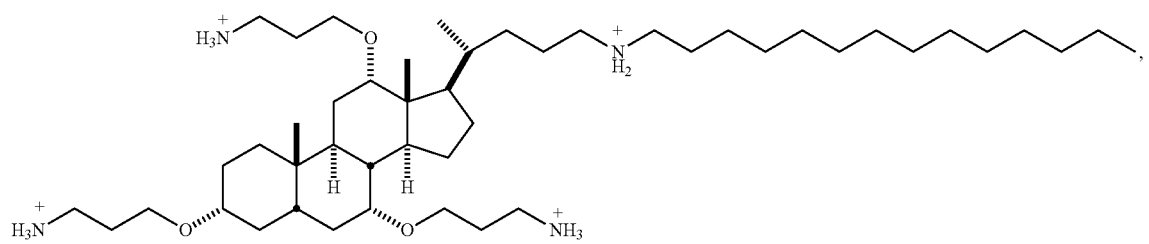
CSA-137
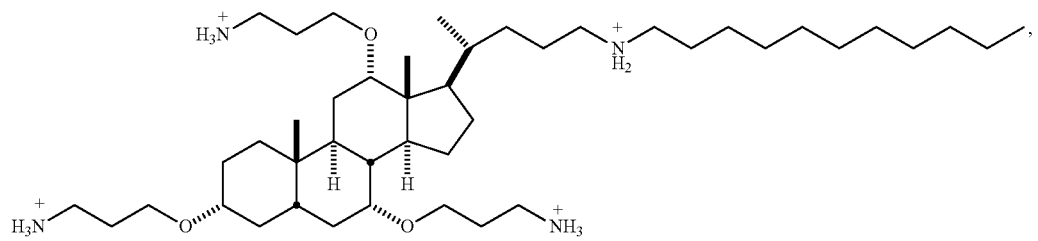
CSA-138
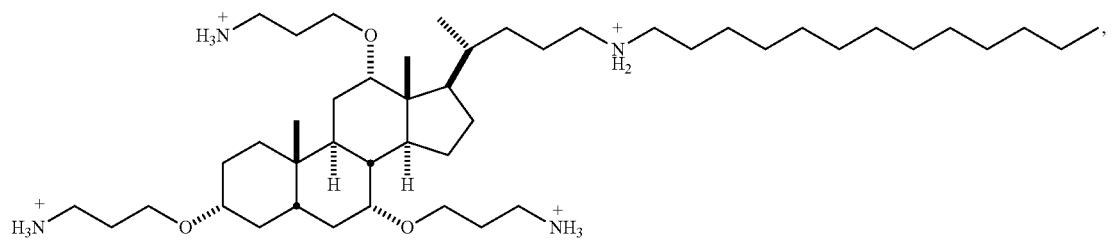
CSA-144
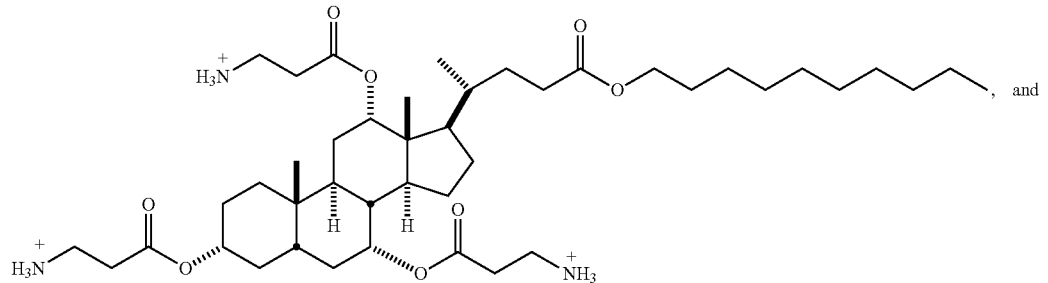
, and

CSA-145

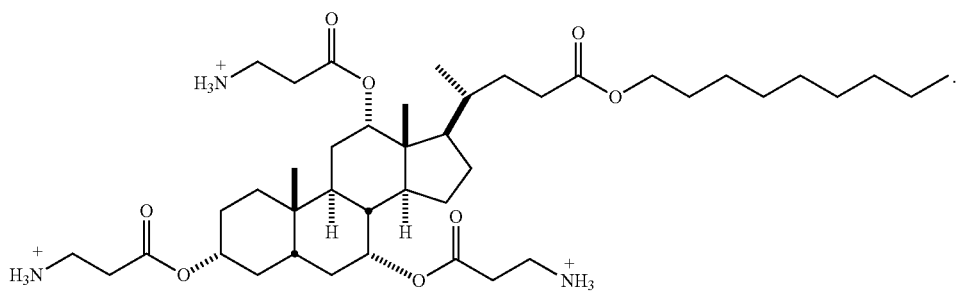

10. A device comprising a polymer structure and the hydrophobic CSA compound of claim 1 incorporated into the polymer structure with non-covalent interactions.

11. The device of claim 10, wherein the polymer structure includes polyvinyl alcohol, sodium polyacrylate, an acrylate polymer, polyethylene oxide, polyAMPS, polyvinylpyrrolidone, polyacrylamide, silicone, agarose, methylcellulose, hyaluronan, or a combination thereof.

12. The device of claim 10, wherein the device comprises a medical device selected from the group consisting of bone implant, bone pin, bone screw, tissue graft, endotracheal tube, coronary stent, peripheral stent, catheter, arterio-venous graft, by-pass graft, pacemaker or defibrillator lead, anastomotic clip, arterial closure device, patent foramen ovale closure device, and drug delivery balloon.

13. The device of claim 10, wherein the polymer is coated on a substrate.

14. The device of claim 10, wherein the hydrophobic CSA compound elutes from the polymer in excess saline water at a rate of 0.1-100 μg/ml, 0.5-50 μg/ml, or 1-10 μg/ml at 3 days, one week, or one month and/or over a period of 3 days, one week and/or one month.

15. A hydrophobic cationic steroidal anti-microbial (CSA) compound comprising:
 a sterol structure comprising four fused carbon rings;
 at least one cationic substituent attached to each of at least three of the four fused carbon rings so as to form an amphiphilic compound having a hydrophobic sterol face and a hydrophilic cationic face;
 at least one hydrophobic substituent attached to at least one of the fused carbon rings;
 wherein the CSA compound has a CLogP value of at least 6.5 and a structure selected from the group consisting of:

CSA-131

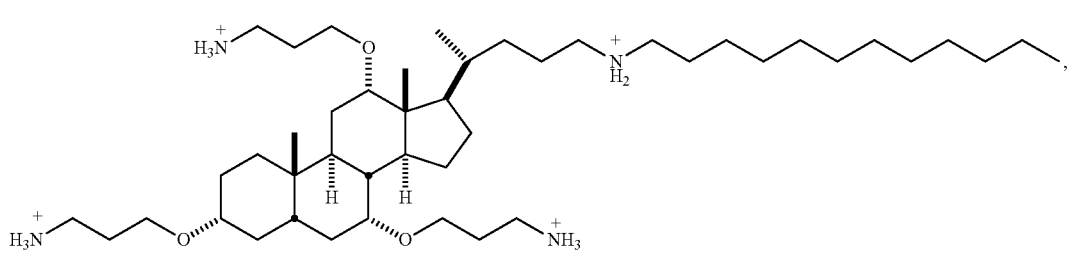

CSA-134

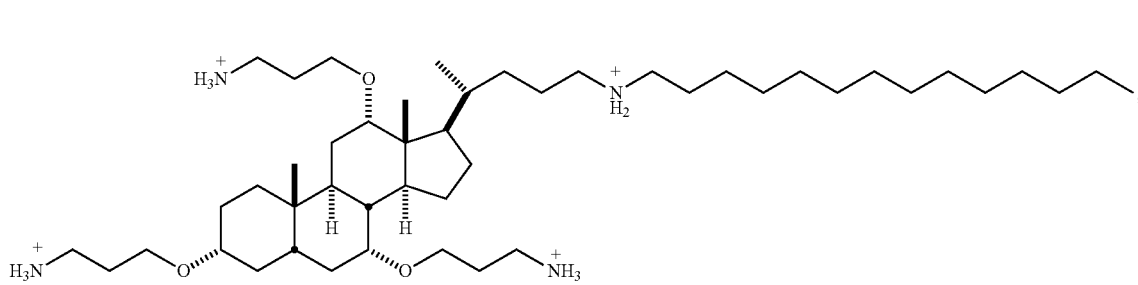

CSA-137

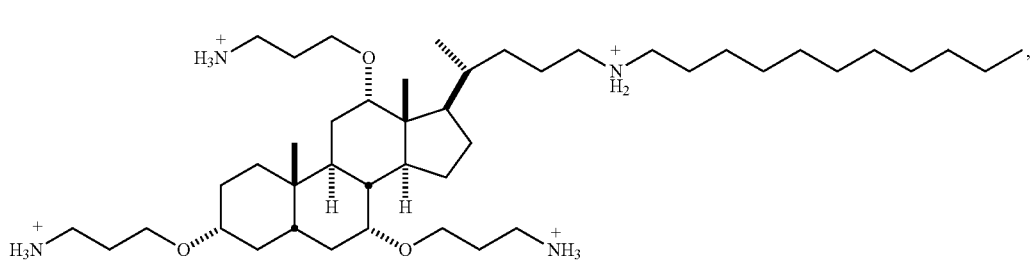

CSA-138
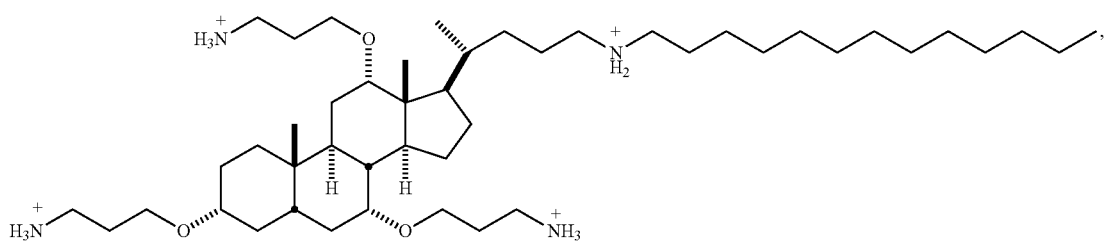

CSA-144
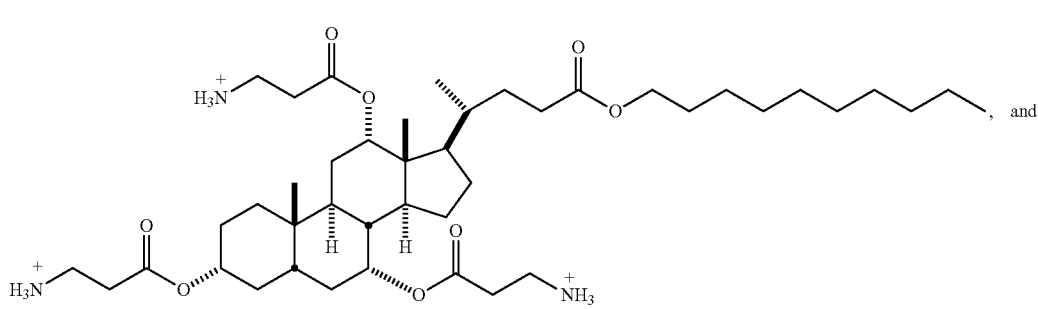
, and

CSA-145
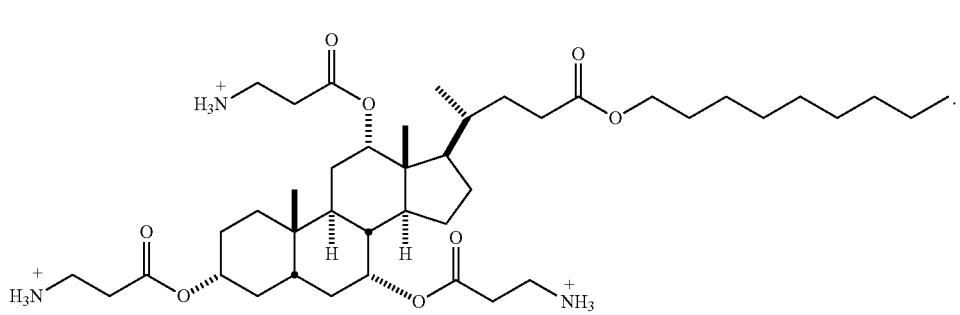
.

16. A device comprising a polymer structure and the hydrophobic CSA compound of claim 15 incorporated into the polymer structure with non-covalent interactions.

17. The device of claim 16, wherein the device comprises a medical device selected from the group consisting of bone implant, bone pin, bone screw, tissue graft, endotracheal tube, coronary stent, peripheral stent, catheter, arterio-venous graft, by-pass graft, pacemaker or defibrillator lead, anastomotic clip, arterial closure device, patent foramen ovale closure device, and drug delivery balloon.

18. A medical device comprising a polymer structure and a hydrophobic cationic steroidal anti-microbial (CSA) compound incorporated into the polymer with non-covalent interactions, the CSA compound comprising:

a sterol structure comprising four fused carbon rings;

at least one cationic substituent attached to each of at least three of the four fused carbon rings so as to form an amphiphilic compound having a hydrophobic sterol face and a hydrophilic cationic face;

at least one hydrophobic substituent attached to at least one of the fused carbon rings;

wherein the CSA compound has a CLogP value of at least 6.5 and a structure as in Formula (1):

Formula (I)
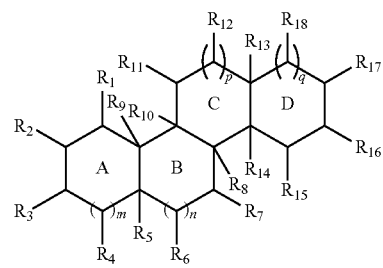

wherein $q=0$ and $p=1$;

$R_3$, $R_7$, and $R_{12}$ independently include a cationic group;

$R_{17}$ is a hydrophobic substituent; and $R_1$, $R_2$, $R_4$-$R_6$, $R_8$-$R_{16}$ are any substituent, with the proviso that $R_{16}$ does not form a fused ring with $R_{17}$.

19. The medical device of claim 18, wherein the polymer structure includes polyvinyl alcohol, sodium polyacrylate, an acrylate polymer, polyethylene oxide, polyAMPS, polyvinylpyrrolidone, polyacrylamide, silicone, agarose, methylcellulose, hyaluronan, or a combination thereof.

20. The medical device of claim 18, wherein the medical device is selected from the group consisting of bone implant, bone pin, bone screw, tissue graft, endotracheal tube, coronary stent, peripheral stent, catheter, arterio-venous graft, by-pass graft, pacemaker or defibrillator lead, anastomotic clip, arterial closure device, patent foramen ovale closure device, and drug delivery balloon.

* * * * *

UNITED STATES PATENT AND TRADEMARK OFFICE
CERTIFICATE OF CORRECTION

PATENT NO.      : 8,975,310 B2  
APPLICATION NO. : 13/554957  
DATED           : March 10, 2015  
INVENTOR(S)     : Savage Page 1 of 1

It is certified that error appears in the above-identified patent and that said Letters Patent is hereby corrected as shown below:

Specifications

Column 1  
Line 50, change "ant-microbial" to --anti-microbial--

Column 4  
Line 48, change "atoms are more is sufficient" to --atoms are sufficient--

Column 8  
Line 38, change "the functional" to --to the functional--

Column 10  
Line 12, change "out service" to --outer surface--  
Line 53, change "elution elution" to --elution--

Signed and Sealed this  
Twenty-sixth Day of April, 2016

Michelle K. Lee  
*Director of the United States Patent and Trademark Office*